US009795651B2

(12) United States Patent
Yoon et al.

(10) Patent No.: US 9,795,651 B2
(45) Date of Patent: Oct. 24, 2017

(54) COMPOSITION FOR INHIBITING HUMAN CYTOMEGALOVIRUS REPLICATION

(71) Applicant: RESEARCH & BUSINESS FOUNDATION SUNGKYUNKWAN UNIVERSITY, Suwon-si (KR)

(72) Inventors: Keejung Yoon, Gwacheon-si (KR); Soobong Ha, Ulsan (KR)

(73) Assignee: Research & Business Foundation Sungkyunkwan University, Suwon-si (KR)

( * ) Notice: Subject to any disclaimer, the term of this patent is extended or adjusted under 35 U.S.C. 154(b) by 0 days.

(21) Appl. No.: 15/013,510

(22) Filed: Feb. 2, 2016

(65) Prior Publication Data

US 2016/0228501 A1 Aug. 11, 2016

(30) Foreign Application Priority Data

Feb. 4, 2015 (KR) ........................ 10-2015-0017213

(51) Int. Cl.
*C12N 15/63* (2006.01)
*A61K 38/17* (2006.01)

(52) U.S. Cl.
CPC .......... *A61K 38/1709* (2013.01); *C12N 15/63* (2013.01)

(58) Field of Classification Search
CPC ................ A61K 48/00–48/0083; C12N 15/63
See application file for complete search history.

(56) References Cited

FOREIGN PATENT DOCUMENTS

WO WO 98/20142 5/1998

OTHER PUBLICATIONS

Kobayashi et al. Expression dynamics of Hes factors in development and disease. Current Topics in Developmental Biology, vol. 110, pp. 263-283, 2014.*
Allman et al. Separation of Notch1 promoted lineage commitment and expansion/transformation in developing T cells. J. Exp. Med. vol. 194, No. 1, pp. 99-106, Jul. 2001.*
Kawamata et al. Overexpression of the notch target genes Hes in vivo induces lymphoid and myeloid alterations. Oncogene, vol. 21, pp. 3855-3863, 2002.*
Weng et al. Activating mutations of NOTCH1 in human T cell acute lymphoblastic leukemia. Science, vol. 306, pp. 269-271, Oct. 2004.*
Kiaris et al. Modulation of notch signaling elicits signature tumors and inhibits hras1-induced oncogenesis in the mouse mammary epithelium. American Journal of Pathology, vol. 165, No. 2, pp. 695-705, Aug. 2004.*
Mo et al. Amplified in breast cancer 1 promotes colorectal cancer progression through enhancing notch signaling. Oncogene, vol. 34, pp. 3935-3945, 2015, published online Sep. 29, 2014.*
Taylor et al. Disrupting NOTCH slows diffuse intrinsic pontine glioma growth, enhances radiation sensitivity, and shows combinaotiral efficacy with bromodomain inhibition. Journal of Neuropathology and Experimental Neurology, vol. 74, No. 8, pp. 778-790, Aug. 2015, printed as pp. 1/23-23/23.*
Guseh et al. Notch signaling promotes airway mucous metaplasia and inhibits alveolar development. Development, vol. 136, pp. 1751-1759, 2009.*
Verma et al. Gene therapy—promises, problems and prospects. Nature, vol. 389, pp. 239-242, 1997.*
Palù et al. In pursuit of new developments for gene therapy of human diseases. Journal of Biotechnology, vol. 68, pp. 1-13, 1999.*
Luo et al. Synthetic DNA delivery systems. Nature Biotechnology, vol. 18, pp. 33-37, 2000.*
Verma and Weitzman, Gene Therapy: Twenty-first century medicine. Annual Review of Biochemistry, vol. 74, pp. 711-738, 2005.*
Ginn et al. Gene therapy clinical trials worldwide to 2012—an update. The Journal of Genetic Medicine, vol. 15, pp. 65-77, 2013.*
Mocarski et al. Human cytomegalovirus in a SCID-hu mouse: thymic epithelial cells are prominent targets of viral replication. Proceedings of the National Academy of Sciences, USA, vol. 90, No. 1, pp. 104-108, Jan. 1993.*
Borggrefe, T., and F. Oswald. "The Notch signaling pathway: transcriptional regulation at Notch target genes." Cellular and molecular life sciences 66.10 (2009): 1631-1646.
Transcription factor HES-5 [*Homo Sapiens*], NCBI Reference Sequence: NP_001010926.1, "http://www.ncbi.nlm.nih.gov/protein/58219048?sat=17&satkey=23462184", Jan. 7, 2013 (2 pages).
Hairy/enhancer-of-split related with YRPW motif protein 2 [*Homo sapiens*], NCBI Reference Sequence: NP_036391.1, http://www.ncbi.nlm.nih.gov/protein/6912414?sat=18&satkey=39422, Oct. 22, 2013.
Transcription factor HES-1 [*Homo sapiens*], NCBI Reference Sequence: NP_005515.1, http://www.ncbi.nlm.nih.gov/protein/5031763?sat=18&satkey=37150, Nov. 3, 2013.
Hairy/enhancer-of-split related with YRPW motif protein 1 isoform b [*Homo sapiens*], NCBI Reference Sequence: NP_001035798.1, http://www.ncbi.nlm.nih.gov/protein/105990526?sat=18&satkey=25498 Nov. 3, 2013.

* cited by examiner

*Primary Examiner* — Jennifer Dunston
(74) *Attorney, Agent, or Firm* — NSIP Law (57) ABSTRACT

Provided is a pharmaceutical composition for inhibiting human cytomegalovirus (HCMV) replication by increasing the expression of a target gene of a notch signaling pathway, for example, hairy and enhancer of split-1 (Hes1), hairy and enhancer of split-5 (Hes5), hairy/enhancer-of-split related with YRPW motif protein 1 (Hey1) and hairy/enhancer-of-split related with YRPW motif protein 2 (Hey2), and a method and use for treating an HCMV infectious disease using the same. The composition of the present invention has an excellent effect in inhibiting the HCMV replication, and therefore a target and a therapeutic agent for preventing or treating various HCMV-related diseases caused by the HCMV infection and a use for treating the HCMV infectious disease may be provided.

8 Claims, 3 Drawing Sheets

COMPOSITION FOR INHIBITING HUMAN CYTOMEGALOVIRUS REPLICATION

CROSS-REFERENCE TO RELATED APPLICATION

This application claims priority to and the benefit of Korean Patent Application No. 10-2015-0017213, filed on Feb. 4, 2015, the disclosure of which is incorporated herein by reference in its entirety.

The present invention was undertaken with the support of Mid-career Researcher Program No. NRF-2015R1A2A2A01005687 grant funded by the Ministry of Science, ICT and future planning.

REFERENCE TO AN ELECTRONIC SEQUENCE LISTING

The contents of the electronic sequence listing (NTCWR20160222_0421350028_Revised SequenceListing.txt; size: 11,294 bytes; created April 21, 2016) is herein incorporated by reference in its entirety.

BACKGROUND

1. Field of the Invention

The present invention relates to a pharmaceutical composition for preventing or treating a human cytomegalovirus (HCMV) infectious disease, which includes a notch-target protein or a gene encoding the same as an active ingredient.

2. Discussion of Related Art

HCMV which is known as herpes virus-5 has a high species specificity with respect to culture cells unlike herpes simplex and is proliferated only in human fetal fibroblasts. Globally occurring in about 1% of new borns, the HCMV infection novel is one of the most common congenital infections, and 40% of the population is infected with the HCMV. About 10 to 15% of the congenital HCMV infections have symptoms, and 50 to 90% of the infections with symptoms have side effects such as mental retardation or sensorineural deafness.

Korea Centers for Disease Control and Prevention says that disease incidences caused by infection are very high in Europe and U.S., and 95% or more of adults in Korea have a disease in a subclinical incubation state, but the disease occurrence in Korea is lower than those of the Europe and the U.S. However, it is known that, in the case of people who get immuno-inhibitor injection after leukemia, a cancer, immunodeficiency and organ transplantation, the incubation state is reactivated causing a disease such as retinitis, infection, or colitis. Particularly, the number of organ transplantation patients in Korea is on the growing trend every year, and thus the importance of a therapeutic agent against HCMV further stands out.

When healthy people are infected with HCMVs, there may be no symptom, but when infants or immuno-deficient patients who have relatively weak immunity, are infected with HCMVs, serious symptoms may develop. Particularly, the HCMVs are known as a cause of further deterioration of malignant tumors including a brain tumor, a colon cancer, a breast cancer, etc.

The HCMVs influence the liver, brain, lung, ears or eyes, and HCMV infectious diseases include pneumonia, cytomegaloviral mononucleosis, cytomegaloviral retinitis, cytomegaloviral hepatitis, cytomegaloviral infection, and cytomegaloviral antigenemia, etc. Until now, as a treatment method for a HCMV infectious disease, the use of an anti HCMV drug, the administration of an antiviral agent, or the administration of an immunoglobulin had been mainly used. However, such conventional treatment methods have an inconvenience of monitoring a period of treating blood and kidney functions or a liver function, and a problem of targeting an HCMV infectious disease other than cancer.

Meanwhile, a notch derived from a gene making a groove of the wing of a drosophila by inducing excessive growth in a notch mutation is a membrane protein structure serving as a cell surface receptor and used for rapid transduction and amplification of a signal between cells in a multicellular animal.

It is reported that the notch signaling is well conserved evolutionarily from vertebrates to invertebrates and plays an important role in determining the destiny of a cell in the early stage of development. The notch signaling is known as a key factor for regulating differentiation of nerves, eyeballs, lymph, muscles, globules, etc. and is involved in haemangiogenesis.

All of a notch receptor and ligands are membrane proteins, and the ligands and the notch receptor are linked between two adjacent cells, thereby realizing notch signaling. After two hydrolyses, in the notch receptor, a notch intracellular domain (NICD) is separated and then transferred to a nucleus. In the nucleus, NICD is a transcription repressor and linked to C-promoter binding factor 1 (CBF-1)/suppressor of hairless/lag-1 (CSL) and thereby replaces a corepressor (CoR) previously linked with the CSL. An NICD/CSL complex collects a co-activator (CoA) such as mastermind-like (MAML) or p300 and thus induces or inhibits notch target genes such as hairy/enhancer of Split (HES), hairy/enhancer-of-split related with YRPW motif protein (HEY), cyclin D1, p21, NF-κB, c-Myc, pre-T cell receptor alpha chain (pre-Tα), GATA3, NRARP and Deltex1. Here, HES is a representative target gene for notch signaling and one of the transcription factors expressed when the notch signaling pathway is activated. A Hes family includes Hes1, Hes3, and Hes5. Also, HEY is a representative notch target gene having an increased expression level by a notch signaling pathway and is included in a Hes-related family.

When such a notch signaling is activated, it is known that tumor occurs in various cancer models. It is known that, when the active notch, NICD, is expressed in a mouse stem cell, T-cell leukemia/lymphomas occurs, and about 50% of activated notch 1 has been found in T-cell acute lymphoblastic leukemia (TALL). Also, it has been reported that the notch receptor and ligands and a target for the notch signaling are activated in various cancers including uterine cervical cancer, lung cancer, pancreatic cancer, ovarian cancer, breast cancer, prostate cancer, and it is known that the notch 1 receptor is associated with a bad prognosis in breast cancer patients and associated with cancer metastasis in a prostate cancer.

For these reasons, studies on notch signaling-associated factors are very important for analyzing the causes of various diseases for humans and finding a treatment method therefor. Particularly, to treat a cancer or an autoimmune disease, the importance of the role of a signaling pathway such as the notch signaling pathway is emphasized.

In addition, to treat cancer or an autoimmune disease, studies on inhibiting notch signaling in various aspects have been performed, and a considerable amount of genes affecting notch signaling were found as a result of the rapid development of a scale genomic search, a proteomic analysis method and bioinformatics.

However, through such a research, the complexity of the notch signaling pathway, the interconnection with another signaling pathway, and particularly, a relationship with HCMVs have not been revealed so far.

SUMMARY OF THE INVENTION

The present invention is directed to providing a novel pharmaceutical composition for inhibiting HCMV replication by a target protein of a notch signaling pathway or a gene encoding the same.

However, technical problems to be solved in the present invention are not limited to the above-described problems, and other problems which are not described herein will be clearly understood by those of ordinary skill in the art from the following descriptions.

In one aspect, the present invention provides a pharmaceutical composition for preventing or treating an HCMV infectious disease, which includes a notch target protein or a gene encoding the same as an active ingredient.

In one exemplary embodiment of the present invention, the notch target protein may be selected from the group consisting of hairy and enhancer of split-1 (Hes1), hairy and enhancer of split-5 (Hes5), hairy/enhancer-of-split related with YRPW motif protein 1 (Hey1), and hairy/enhancer-of-split related with YRPW motif protein 2 (Hey2).

In another exemplary embodiment of the present invention, the HCMV infectious disease may be selected from the group consisting of a brain tumor, a colon cancer, a breast cancer, pharyngitis and pneumonia.

In still another exemplary embodiment of the present invention, the Hes1 protein may consist of an amino acid sequence of SEQ ID NO: 1.

In yet another exemplary embodiment of the present invention, the Hes5 protein may consist of an amino acid sequence of SEQ ID NO: 2.

In yet another exemplary embodiment of the present invention, the Hey1 protein may consist of an amino acid sequence of SEQ ID NO: 3.

In yet another exemplary embodiment of the present invention, the Hey2 protein may consist of an amino acid sequence of SEQ ID NO: 4.

In another aspect, the present invention provides a method of preventing or treating an HCMV infectious disease, which includes administering a pharmaceutical composition including a pharmaceutically effective amount of an HCMV replication inhibitor to an individual.

In still another aspect, the present invention provides a method of preventing or treating an HCMV infectious disease using a pharmaceutical composition including an HCMV replication inhibitor.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Exemplary embodiments of the present invention will be described in detail below with reference to the accompanying drawings. While the present invention is shown and described in connection with exemplary embodiments thereof, it will be apparent to those skilled in the art that various modifications can be made without departing from the spirit and scope of the invention.

The present invention provides a pharmaceutical composition for inhibiting a HCMV replication by a target gene of a notch signaling pathway.

In one exemplary embodiment of the present invention, when HFF cells are infected with HCMVs, qRT-PCR and western blotting were performed to examine a transcription level of a notch target gene and an expression level of the notch target protein by the HCMV infection, respectively (refer to Examples 1 and 2). Also, the influence of the notch target gene on the HCMV replication was examined (refer to Example 3).

In the present invention, to express the notch target gene such as Hes1, Hes5, Hey1 or Hey2 in the HFF cells, a retrovirus vector was used. The retrovirus vector is integrated into intracellular genetic materials when the cells are infected with the vector, and thereby a stable cell line expressing the gene may be formed.

As a result, it was shown that there is an effect of inhibiting the HCMV replication in the HFF cells expressing the notch target genes. Therefore, the notch target protein or the gene encoding the same of the present invention may be used to prevent or treat an HCMV infectious disease.

The notch target protein may be selected from the group consisting of hairy and enhancer of split-1 (Hes1), hairy and enhancer of split-5 (Hes5), hairy/enhancer-of-split related with YRPW motif protein 1 (Hey1) and hairy/enhancer-of-split related with YRPW motif protein 2 (Hey2), but the present invention is not limited thereto.

Also, the HCMV infectious disease may be selected from the group consisting of a brain tumor, a colon cancer, a breast cancer, pharyngitis and pneumonia, but the present invention is not limited thereto.

In addition, the Hes1, Hes5, Hey1 and Hey2 proteins may consist of amino acid sequences of SEQ ID NOs: 1, 2, 3 and 4, respectively, but the present invention is not limited thereto.

The term "treatment" used herein means that the symptoms caused by an HCMV infectious disease are relieved or beneficially changed through the administration of the pharmaceutical composition according to the present invention.

Therefore, to prepare the pharmaceutical composition, suitable carrier, excipient and diluent which are conventionally used may be additionally included. Also, the pharmaceutical composition may be prepared in a form such as an oral preparation, a preparation for an external use, a suppository or a sterile injection, for example, a powder, a granule, a tablet, a capsule, a suspension, an emulsion, a syrup or an aerosol, through a conventional method of administration.

As a carrier, excipient and diluent that can be included in the composition, lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, mineral oil, etc. are used. When the composition is formulated, a diluent or excipient such as a filler, a thickener, a binder, a wetting agent, a disintegrating agent or a surfactant is generally used.

The pharmaceutical composition according to the present invention is administered in a pharmaceutically effective amount. The term "pharmaceutically effective amount" used herein refers to an amount sufficient to treat the disease at a reasonable benefit/risk ratio applicable for a medical treatment, and the level of an effective dosage may be determined by parameters including a type of illness of a patient, severity, the activity of a drug, sensitivity to a drug, administration time, an administration route and a release rate, duration of treatment and co-used drugs, and other parameters well known in medical fields.

The pharmaceutical composition according to the present invention may be simultaneously, separately or sequentially administered with a co-used drug to improve a treating effect and may be administered once or multiple times. It is important to administer the least amount with which the greatest effect is obtained without a side effect in consideration of all of the above-described parameters, and the amount may be easily determined by those of ordinary skill in the art. Specifically, the effective amount of the pharmaceutical composition according to the present invention may depend on the age, sex, condition and body weight of a patient, an absorption rate, inactivity and a release rate of an active component in the body, the type of a disease, or co-used drugs.

The pharmaceutical composition of the present invention may be administered by various routes. Every administration method can be expected, and thus the pharmaceutical composition of the present invention may be administered by, for example, oral administration, intranasal administration, intratracheal administration, intra-arterial injection, intravenous injection, subcutaneous injection, muscular injection, or intraperitoneal injection. The pharmaceutical composition of the present invention may be administered at a dose of about 0.0001 to 100 mg/kg, and preferably, 0.001 to 10 mg/kg per day once to several times, but the present invention is not limited thereto.

The pharmaceutical composition of the present invention is determined by the type of a drug that is an active ingredient in addition to various related parameters including a disease to be treated, an administration route, age, sex or a body weight of a patient, and a severity of the disease.

In still another aspect, the present invention provides a method of treating an HCMV infectious disease, which includes administering the pharmaceutical composition of the present invention into an individual.

The term "individual" used herein means a subject with a disease to be treated and more particularly, a human or non-human primate and a mammal such as a mouse, a rat, a dog, a cat, a horse, and a cow.

Further, in yet another aspect, the present invention provides a use of the pharmaceutical composition to prevent or treat an HCMV infectious disease.

Hereinafter, exemplary examples will be presented to help in understanding the present invention. However, the following examples are merely provided to more easily understand the present invention, but the scope of the present invention is not limited to the following examples.

EXAMPLES

Example 1

Experimental Methods

Cell Culture HFF cells with passage numbers 16 to 20 were used. The HFF cells were cultured in a Dulbecco's modified Eagle's medium (DMEM) supplemented with 10% fetal bovine serum (FBS) in a 37° C., 5% $CO_2$ environment.

Viral Infection

The HFF cells which were host cells were infected with HCMV at a multiplicity of infection (MOI) of 0.01, and the medium was replaced with fresh medium every third day until the HCMV infection occurred on all of the cells. Afterward, it was confirmed that all of the cells were infected with the HCMVs, and then HCMVs were obtained by harvesting a supernatant. The titer of the obtained HCMVs was performed through immunocytochemistry (ICC) using 1E1/2, and the HFF cells were aliquoted, grown to about 90%, and then infected with HCMV.

Quantitative Real Time PCR (qRT-PCR)

Total RNA was isolated using a TRIZOL reagent. 500 ng of cDNA per sample was synthesized from the isolated RNA using oligo dT primers and a moloney murine leukemia virus-reverse transcriptase (MMLV-RT), and qRT-PCR was performed using the primer described in the following Example 2-1.

Western Blotting

The HFF cells were lysed with an RIPA buffer containing PMSF which is a protease inhibitor. Protein samples of equal amounts were loaded on an SDS-PAGE gel and then transferred onto a PVDF membrane. The transferred gel was blocked by adding 5% skim milk to TBST (150 mM NaCl, 10 mM Tris/HCl, 0.1% (v/v) Tween 20, pH 8.0). Afterward, a protein expression was confirmed using an antibody with respect to a target protein.

Immunocytochemistry (ICC)

The HFF cells were fixed using 4% PFA and permeablized with 100% ethanol. Afterward, as an antibody with respect to the target protein, the expression of IE 1/2 was confirmed.

Example 2

Expression of Notch Target Gene by HCMV Infection 2-1. Examination of Expression Level of Notch Target Gene: mRNA Level When the HFF cells were infected with HCMVs, the expression levels of the notch target genes were examined in terms of mRNA levels.

The HFF cells with a passage number 18 were infected with HCMVs at MOI of 0 or 5, and 5 heat inactivation (HI), and 72 hours later, RNA was isolated with TRIZOL. The isolated RNA was reacted with oligo dT primers and MMLV-RT to synthesize 500 ng of cDNA per sample. The synthesized cDNA was subjected to qRT-PCR with notch target gene primers, and the mRNA expressions of the notch target genes were compared. The primers used in the qRT-PCR are as follows:

```
Hes1
                                    (SEQ ID NO: 5)
F primer:    5'-GAAGCACCTCCGGAACC-3'

(SEQ ID NO: 6)
R primer:    5'-GTCACCTCGTTCATGCACTC-3'

Hes5
                                    (SEQ ID NO: 7)
F primer:    5'-TCAGCCCCAAAGAGAAAAAC-3'

(SEQ ID NO: 8)
R primer:    5'-TAGTCCTGGTGCAGGCTCTT-3'

Hey1
                                    (SEQ ID NO: 9)
F primer:    5'-ACG AGA CCG GAT CAA TAA CA-3'

(SEQ ID NO: 10)
R primer:    5'-ATC CCA AAC TCC GAT AGT CC-3'

Hey2
                                    (SEQ ID NO: 11)
F primer:    5'-GCA CTC TCG GAA TCC TAT GC-3'

(SEQ ID NO: 12)
R primer:    5'-CGT CGG GAT CGG ATA AAT AA-3'
```

Figure 1:
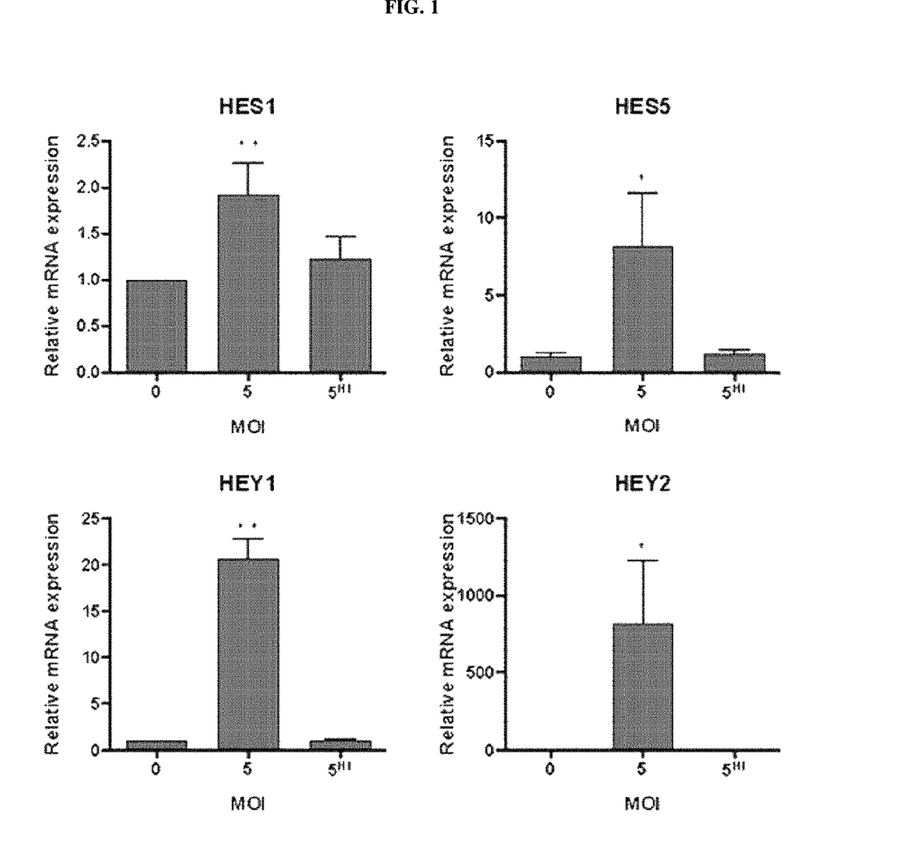
FIG. 1 shows comparison results for mRNA expression levels of notch target genes by HCMV infections in human foreskin fibroblast (HFF) cells.

Consequently, as shown in FIG. 1, it can be confirmed the expressions of the notch target genes such as Hes1, Hes5, Hey1 and Hey2 were increased by the HCMV infection. Therefore, it can be seen that the expression levels of the notch target genes in the host cells are increased by the HCMV infection.

Also, it was confirmed that the increased expression of the notch target genes disappears in a negative control (HI) from which viral infectivity was removed through a thermal treatment of HCMVs at 56° C. for 30 minutes, and from this, it can be seen that the increase in expression of the notch target genes by HCMV is caused by an HCMV viral gene through the infection in the HCMV cells, not by the contact between the HCMVs and the host cells.

2-2. Examination of Expression Level of Notch Target Protein: Protein Level

When the HFF cells were infected with HCMVs, the expression levels of the notch target genes were examined in terms of protein levels.

The HFF cells with a passage number of 18 were infected with HCMVs at MOI of 0 or 5, and 5 heat inactivation (HI), and 72 hours later, the cells were lysed. The lysis was performed using an RIPA buffer, and a protease inhibitor was added. Western blotting (12.5% SDS PAGE gel, 100 mA transfer/membrane 50 min, 5% skim milk blocking RT 1 hr, a primary Ab (Rb anti Hes1, 1:500, 4'C O/N), a secondary Ab (anti Rb IgG HRP, 1:10000, RT 2hr), ATTO ECL solution develop) was performed on the protein samples obtained through the lysis to compare the expression of Hes1 gene. Simply, the protein samples were loaded on an SDS PAGE gel, the proteins were transferred onto a PVDF membrane, and then the protein expression was confirmed using an anti-Hes1 antibody.

Figure 2:
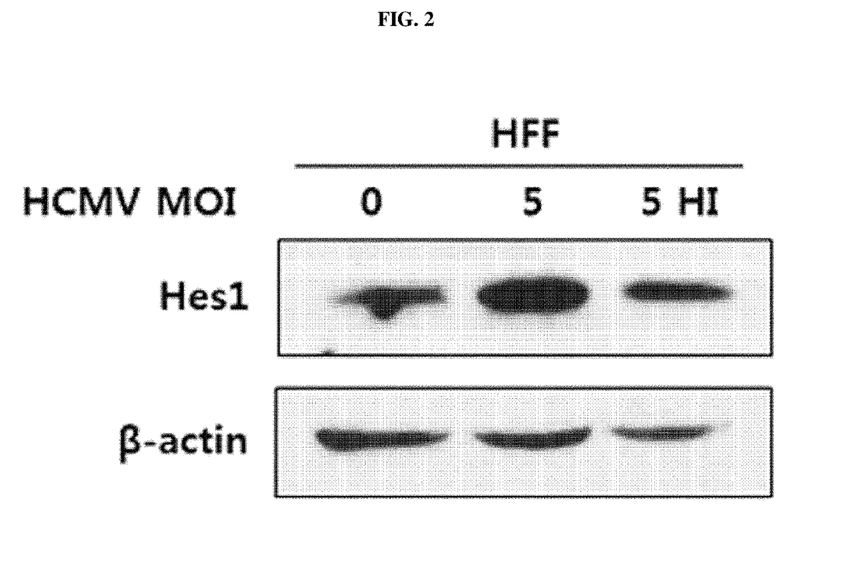
FIG. 2 shows western blotting results of comparative levels of Hes1 protein expression due to a HCMV infection in HFF cells.

Consequently, as shown in FIG. 2, it can be confirmed that the expression of the protein expressed by the notch target gene Hest was increased by the HCMV infection. Therefore, as shown in the above RNA expression experiment in Example 2-1, it can be seen that the expression level of the Hest protein was increased by the HCMVs, but such an increase in Hest protein expression level was not observed in the thermally-treated HCMVs (HI).

Accordingly, it can be confirmed that the HCMV infection increases not only the levels of the RNA of the notch target gene but also the protein expression.

Example 3

Confirmation of HCMV Inhibitory Effect by Notch Target Gene

When the HFF cells were infected with the HCMVs, progeny viruses were produced through productive replication. An experiment for analyzing the influence of the notch target gene on the HCMV replication was performed using such a phenomenon.

The notch target gene was expressed in the HFF cells with a passage number of 17 using a retrovirus and infected with the HCMVs. As a control, HFF cells expressing a green fluorescence protein (GFP) were used. The progeny HCMVs produced in the HFF cells were obtained by infection time, and then novel HFF cells were infected with the progeny HCMVs, thereby obtaining media containing the HCMVs produced by time. Subsequently, the influence of the notch target genes on the HCMV replication was confirmed. To confirm the influence of the notch target genes on the HCMV replication, novel HFF cells were infected with the HCMVs, and the next day, the amount of the progeny HCMVs were detected through ICC using an HCMV viral gene, which is an anti-IE1/2 antibody. The HFF cells were fixed with 4% PFA and permeablized with 100% ethanol. Afterward, the expression of IE1/2 was confirmed using the antibodies listed below. The antibodies used in ICC are as follows:

Rb anti Hes1, Millipore 1:500
Anti Rb IgG HRP, Abcam, 1:10000
Rb anti IE1/2, LabFrontier, 1:1000
Anti b-actin, Sigma, 1:10000
(compared to 1' Ab, Rb anti IE1/2, 1:1000>2' Ab: anti Rb IgG 555, 1:1000)

Figure 3:
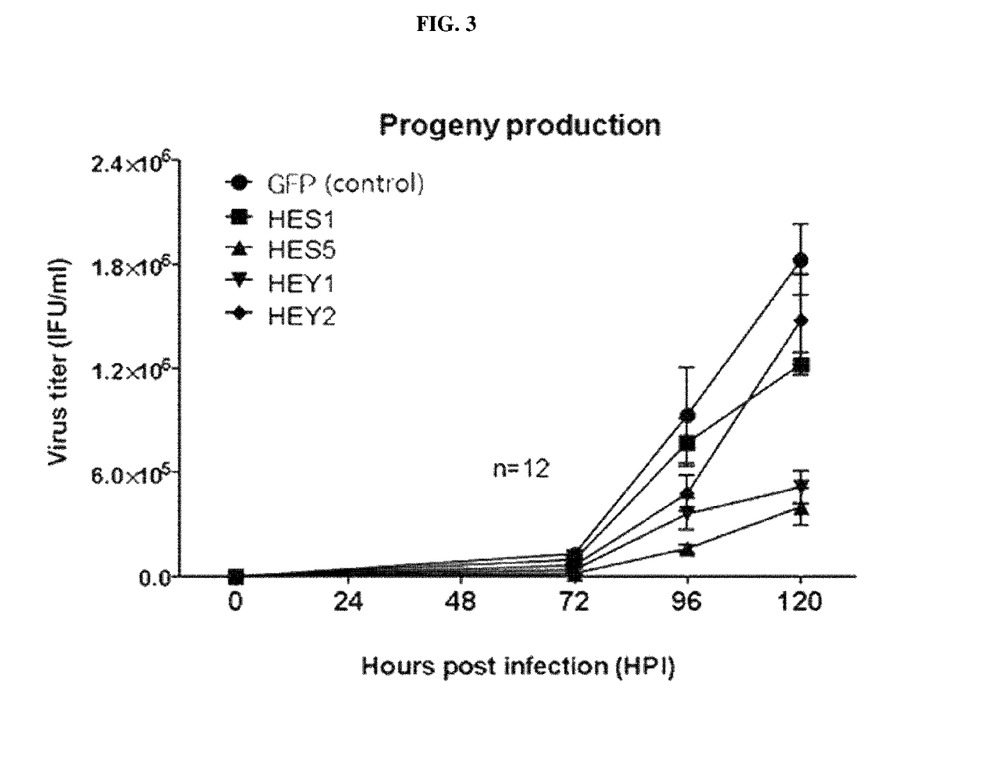
FIG. 3 shows the effect of inhibiting HCMV progeny virus replication caused by the expression of a notch target gene in HFF cells.

Consequently, as shown in FIG. 3, compared to the control (GFP), it was confirmed that the HCMV replication was inhibited in the HFF cells expressing the notch target genes, and particularly, the inhibition of the HCMV replication is remarkably shown in HFF cells overexpressing Hes5 and Hey1.

Therefore, it was seen that the increase in expression of the notch target gene is effective in inhibiting the HCMV replication and was confirmed that the expression of the notch target gene is increased in the HCMV infection by a defense mechanism of the host cell against the HCMVs.

It was confirmed that a pharmaceutical composition according to the present invention, which includes a notch target protein or a gene encoding the same, and an HCMV replication inhibitor as active ingredients, is effective in inhibiting an HCMV replication when a host cell is infected with HCMVs. Accordingly, the pharmaceutical composition is expected to be used in prevention and treatments for all of HCMV infectious diseases including a brain tumor (neuroblastoma or glioblastoma), a breast cancer, a liver cancer, a colon cancer, pharyngitis, or pneumonia by effectively inhibiting the viral replication of HCMVs using the notch target gene.

It would be understood by those of ordinary skill in the art that the above descriptions of the present invention are exemplary, and the exemplary embodiments disclosed herein can be easily modified into other specific forms without changing the technical spirit or essential features of the present invention. Therefore, it should be interpreted that the exemplary embodiments described above are exemplary in all aspects, and are not limitative.

What is claimed is:

1. A method of inhibiting human cytomegalovirus (HCMV) replication, comprising:
   administering a gene encoding a notch target protein to a human cell culture in an amount effective to inhibit HCMV replication, wherein the notch target protein is hairy and enhancer of split-5 (Hes5).

2. The method of claim 1, wherein the Hes5 protein consists of the sequence of SEQ ID NO: 2.

3. A method of inhibiting human cytomegalovirus (HCMV) replication, comprising:
   administering a gene encoding a notch target protein to a human cell culture in an amount effective to inhibit HCMV replication, wherein the notch target protein is hairy and enhancer of split-1 (Hes1).

4. The method of claim 3, wherein the Hes1 protein consists of the sequence of SEQ ID NO: 1.

5. A method of inhibiting human cytomegalovirus (HCMV) replication, comprising:
   administering a gene encoding a notch target protein to a human cell culture in an amount effective to inhibit HCMV replication, wherein the notch target protein is hairy/enhancer-of-split related with YRPW motif protein 1 (Hey1).

6. The method of claim 1, wherein the Hey 1 protein consists of the sequence of SEQ ID NO: 3.

7. A method of inhibiting human cytomegalovirus (HCMV) replication, comprising:
   administering a gene encoding a notch target protein to a human cell culture in an amount effective to inhibit HCMV replication, wherein the notch target protein is hairy/enhancer-of-split related with YRPW motif protein 2 (Hey2).

8. The method of claim 7, wherein the Hey2 protein consists of the sequence of SEQ ID NO: 4.

* * * * *

SEQUENCE LISTING

<160> NUMBER OF SEQ ID NOS: 12

<210> SEQ ID NO 1
<211> LENGTH: 280
<212> TYPE: PRT
<213> ORGANISM: Homo sapiens

<400> SEQUENCE: 1

Met Pro Ala Asp Ile Met Glu Lys Asn Ser Ser Pro Val Ala Ala
1               5                   10                  15

Thr Pro Ala Ser Val Asn Thr Thr Pro Asp Lys Pro Lys Thr Ala Ser
            20                  25                  30

Glu His Arg Lys Ser Ser Lys Pro Ile Met Glu Lys Arg Arg Arg Ala
            35                  40                  45

Arg Ile Asn Glu Ser Leu Ser Gln Leu Lys Thr Leu Ile Leu Asp Ala
        50                  55                  60

Leu Lys Lys Asp Ser Ser Arg His Ser Lys Leu Glu Lys Ala Asp Ile
65                  70                  75                  80

Leu Glu Met Thr Val Lys His Leu Arg Asn Leu Gln Arg Ala Gln Met
                85                  90                  95

Thr Ala Ala Leu Ser Thr Asp Pro Ser Val Leu Gly Lys Tyr Arg Ala
            100                 105                 110

Gly Phe Ser Glu Cys Met Asn Glu Val Thr Arg Phe Leu Ser Thr Cys
        115                 120                 125

Glu Gly Val Asn Thr Glu Val Arg Thr Arg Leu Leu Gly His Leu Ala
    130                 135                 140

Asn Cys Met Thr Gln Ile Asn Ala Met Thr Tyr Pro Gly Gln Pro His
145                 150                 155                 160

Pro Ala Leu Gln Ala Pro Pro Pro Pro Pro Gly Pro Gly Gly Pro
            165                 170                 175

Gln His Ala Pro Phe Ala Pro Pro Pro Leu Val Pro Ile Pro Gly
            180                 185                 190

Gly Ala Ala Pro Pro Pro Gly Gly Ala Pro Cys Lys Leu Gly Ser Gln
            195                 200                 205

Ala Gly Glu Ala Ala Lys Val Phe Gly Gly Phe Gln Val Val Pro Ala
    210                 215                 220

Pro Asp Gly Gln Phe Ala Phe Leu Ile Pro Asn Gly Ala Phe Ala His
225                 230                 235                 240

Ser Gly Pro Val Ile Pro Val Tyr Thr Ser Asn Ser Gly Thr Ser Val
                245                 250                 255

Gly Pro Asn Ala Val Ser Pro Ser Ser Gly Pro Ser Leu Thr Ala Asp
            260                 265                 270

Ser Met Trp Arg Pro Trp Arg Asn
    275                 280

<210> SEQ ID NO 2
<211> LENGTH: 166
<212> TYPE: PRT
<213> ORGANISM: Homo sapiens

<400> SEQUENCE: 2

Met Ala Pro Ser Thr Val Ala Val Glu Leu Leu Ser Pro Lys Glu Lys
1               5                   10                  15

Asn Arg Leu Arg Lys Pro Val Val Glu Lys Met Arg Arg Asp Arg Ile
            20                  25                  30

Asn Ser Ser Ile Glu Gln Leu Lys Leu Leu Leu Glu Gln Glu Phe Ala

```
            35                  40                  45
Arg His Gln Pro Asn Ser Lys Leu Glu Lys Ala Asp Ile Leu Glu Met
     50                  55                  60
Ala Val Ser Tyr Leu Lys His Ser Lys Ala Phe Val Ala Ala Ala Gly
 65                  70                  75                  80
Pro Lys Ser Leu His Gln Asp Tyr Ser Glu Gly Tyr Ser Trp Cys Leu
                 85                  90                  95
Gln Glu Ala Val Gln Phe Leu Thr Leu His Ala Ala Ser Asp Thr Gln
            100                 105                 110
Met Lys Leu Leu Tyr His Phe Gln Arg Pro Ala Ala Pro Ala Ala
        115                 120                 125
Pro Ala Lys Glu Pro Lys Ala Pro Gly Ala Ala Pro Pro Ala Leu
    130                 135                 140
Ser Ala Lys Ala Thr Ala Ala Ala Ala Ala His Gln Pro Ala Cys
145                 150                 155                 160
Gly Leu Trp Arg Pro Trp
                165

<210> SEQ ID NO 3
<211> LENGTH: 308
<212> TYPE: PRT
<213> ORGANISM: Homo sapiens

<400> SEQUENCE: 3

Met Lys Arg Ala His Pro Glu Tyr Ser Ser Ser Asp Ser Glu Leu Asp
 1               5                  10                  15
Glu Thr Ile Glu Val Glu Lys Glu Ser Ala Asp Glu Asn Gly Asn Leu
                20                  25                  30
Ser Ser Ala Leu Gly Ser Met Ser Pro Thr Thr Ser Ser Gln Ile Leu
            35                  40                  45
Ala Arg Lys Arg Arg Arg Gly Ile Ile Glu Lys Arg Arg Arg Asp Arg
     50                  55                  60
Ile Asn Asn Ser Leu Ser Glu Leu Arg Arg Leu Val Pro Ser Ala Phe
 65                  70                  75                  80
Glu Lys Gln Val Met Gln Gly Ser Ala Lys Leu Glu Lys Ala Glu
                85                  90                  95
Ile Leu Gln Met Thr Val Asp His Leu Lys Met Leu His Thr Ala Gly
            100                 105                 110
Gly Lys Gly Tyr Phe Asp Ala His Ala Leu Ala Met Asp Tyr Arg Ser
        115                 120                 125
Leu Gly Phe Arg Glu Cys Leu Ala Glu Val Ala Arg Tyr Leu Ser Ile
    130                 135                 140
Ile Glu Gly Leu Asp Ala Ser Asp Pro Leu Arg Val Arg Leu Val Ser
145                 150                 155                 160
His Leu Asn Asn Tyr Ala Ser Gln Arg Glu Ala Ala Ser Gly Ala His
                165                 170                 175
Ala Gly Leu Gly His Ile Pro Trp Gly Thr Val Phe Gly His His Pro
            180                 185                 190
His Ile Ala His Pro Leu Leu Leu Pro Gln Asn Gly His Gly Asn Ala
        195                 200                 205
Gly Thr Thr Ala Ser Pro Thr Glu Pro His His Gln Gly Arg Leu Gly
    210                 215                 220
Ser Ala His Pro Glu Ala Pro Ala Leu Arg Ala Pro Pro Ser Gly Ser
225                 230                 235                 240
```

```
Leu Gly Pro Val Leu Pro Val Val Thr Ser Ala Ser Lys Leu Ser Pro
                245                 250                 255

Pro Leu Leu Ser Ser Val Ala Ser Leu Ser Ala Phe Pro Phe Ser Phe
            260                 265                 270

Gly Ser Phe His Leu Leu Ser Pro Asn Ala Leu Ser Pro Ser Ala Pro
        275                 280                 285

Thr Gln Ala Ala Asn Leu Gly Lys Pro Tyr Arg Pro Trp Gly Thr Glu
    290                 295                 300

Ile Gly Ala Phe
305

<210> SEQ ID NO 4
<211> LENGTH: 337
<212> TYPE: PRT
<213> ORGANISM: Homo sapiens

<400> SEQUENCE: 4

Met Lys Arg Pro Cys Glu Glu Thr Thr Ser Glu Ser Asp Met Asp Glu
1               5                   10                  15

Thr Ile Asp Val Gly Ser Glu Asn Asn Tyr Ser Gly Gln Ser Thr Ser
            20                  25                  30

Ser Val Ile Arg Leu Asn Ser Pro Thr Thr Thr Ser Gln Ile Met Ala
        35                  40                  45

Arg Lys Lys Arg Arg Gly Ile Ile Glu Lys Arg Arg Arg Asp Arg Ile
    50                  55                  60

Asn Asn Ser Leu Ser Glu Leu Arg Arg Leu Val Pro Thr Ala Phe Glu
65                  70                  75                  80

Lys Gln Gly Ser Ala Lys Leu Glu Lys Ala Glu Ile Leu Gln Met Thr
                85                  90                  95

Val Asp His Leu Lys Met Leu Gln Ala Thr Gly Gly Lys Gly Tyr Phe
            100                 105                 110

Asp Ala His Ala Leu Ala Met Asp Phe Met Ser Ile Gly Phe Arg Glu
        115                 120                 125

Cys Leu Thr Glu Val Ala Arg Tyr Leu Ser Ser Val Glu Gly Leu Asp
    130                 135                 140

Ser Ser Asp Pro Leu Arg Val Arg Leu Val Ser His Leu Ser Thr Cys
145                 150                 155                 160

Ala Thr Gln Arg Glu Ala Ala Met Thr Ser Ser Met Ala His His
                165                 170                 175

His His Pro Leu His Pro His His Trp Ala Ala Ala Phe His His Leu
            180                 185                 190

Pro Ala Ala Leu Leu Gln Pro Asn Gly Leu His Ala Ser Glu Ser Thr
        195                 200                 205

Pro Cys Arg Leu Ser Thr Thr Ser Glu Val Pro Pro Ala His Gly Ser
    210                 215                 220

Ala Leu Leu Thr Ala Thr Phe Ala His Ala Asp Ser Ala Leu Arg Met
225                 230                 235                 240

Pro Ser Thr Gly Ser Val Ala Pro Cys Val Pro Pro Leu Ser Thr Ser
                245                 250                 255

Leu Leu Ser Leu Ser Ala Thr Val His Ala Ala Ala Ala Ala Ala Thr
            260                 265                 270

Ala Ala Ala His Ser Phe Pro Leu Ser Phe Ala Gly Ala Phe Pro Met
        275                 280                 285

Leu Pro Pro Asn Ala Ala Ala Val Ala Ala Ala Thr Ala Ile Ser
    290                 295                 300
```

```
Pro Pro Leu Ser Val Ser Ala Thr Ser Ser Pro Gln Gln Thr Ser Ser
305                 310                 315                 320

Gly Thr Asn Asn Lys Pro Tyr Arg Pro Trp Gly Thr Glu Val Gly Ala
                325                 330                 335

Phe

<210> SEQ ID NO 5
<211> LENGTH: 17
<212> TYPE: DNA
<213> ORGANISM: Artificial Sequence
<220> FEATURE:
<223> OTHER INFORMATION: primer

<400> SEQUENCE: 5
gaagcacctc cggaacc                                                  17

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
gtcacctcgt tcatgcactc                                               20

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
tcagccccaa agagaaaaac                                               20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
tagtcctggt gcaggctctt                                               20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
acgagaccgg atcaataaca                                               20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
```

```
atcccaaact ccgatagtcc                                                    20

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
gcactctcgg aatcctatgc                                                    20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
cgtcgggatc ggataaataa                                                    20
```